US006492541B2

(12) United States Patent
Drauz et al.

(10) Patent No.: US 6,492,541 B2
(45) Date of Patent: Dec. 10, 2002

(54) PROCESS FOR THE PREPARATION OF 3-AMINO-2-OXO-PYRROLIDINES, NOVEL INTERMEDIATES AND THEIR USE

(75) Inventors: Karlheinz Drauz, Freigericht (DE); Günter Knaup, Bruchköbel (DE); Michael Schwarm, Alzenau (DE)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 10/005,817

(22) Filed: Dec. 7, 2001

(65) Prior Publication Data
US 2002/0045763 A1 Apr. 18, 2002

Related U.S. Application Data

(62) Division of application No. 09/860,568, filed on May 21, 2001, now abandoned, which is a division of application No. 09/316,150, filed on May 21, 1999, now Pat. No. 6,281,364.

(30) Foreign Application Priority Data

May 22, 1998 (DE) .......................... 198 22 912

(51) Int. Cl.⁷ ............................. C07C 309/63

(52) U.S. Cl. ...................................... 558/50

(58) Field of Search ............................. 548/550, 518; 546/250, 278.4; 549/497; 558/50

(56) References Cited

U.S. PATENT DOCUMENTS

| 4,012,519 A | 3/1977 | Chan |
| 4,460,603 A | 7/1984 | Chan |
| 6,281,364 B1 * | 8/2001 | Drauz et al. ............ 548/543 |

OTHER PUBLICATIONS

K. Undheim, G. A. Ulsaker: "N–Quaternary Compounds", Acta Chem. Scand., Bd. 27, Nr. 3, 1973, Seiten 1059–1066, XP002111925.
B.E. Evans et al.: "Nanomolar–affinity, Non–Peptide Oxytocin Receptor antagonists", J. Med. Chem., Bd. 36, Nr. 25, 1993, Seiten 3993–4005 XP002111926.

(List continued on next page.)

*Primary Examiner*—Alan L. Rotman
*Assistant Examiner*—Golam M M Shameem
(74) *Attorney, Agent, or Firm*—Pillsbury Winthrop LLP

(57) ABSTRACT

The present invention relates to a process for the preparation of γ-lactams of the general formula I

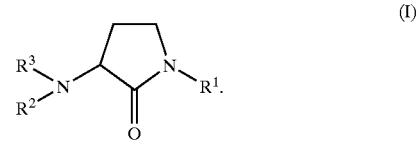

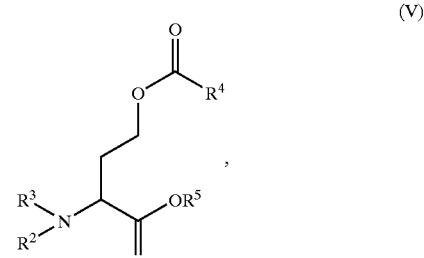

The invention relates also to novel advantageous intermediates of the general formulae V, IV and II and their salts

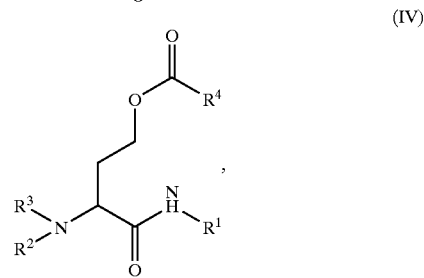

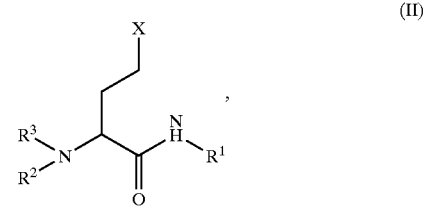

and their use.

The compounds of the general formula I are obtained by cyclising compounds of the general formula II

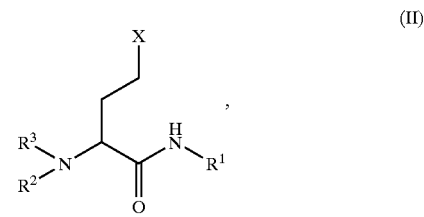

which can be prepared from the intermediate compounds V.

4 Claims, No Drawings

OTHER PUBLICATIONS

G. J. Koomen et al.: "Unconventional Nucleotide Analogues. Part X. Synthesis of N–Substituted 3–(Adenin–9–yl)pyrrolidin–2–ones", J. Chem. Soc. Perkin Trans. 1, 1973, Seiten 1934–1940, XP002111927.

Z. Prochazka et al.: "Synthesis and some biological properties of analogue of angiotensin with modified proline structure", Collect. Czech. Chem. Commun., Bd. 55, Nr. 12, 1990, Seiten 3008–3014, XP002111928.

R. M. Freidinger et al.: "Protected Lactam–Bridged Dipeptides for the Use as Coformational Constraints in Peptides", J. Org. Chem., Bd. 47 Nr. 1, 1982, Seiten 104–109, XP002111929.

G. Cavicchioni et al.: "Synthesis and Biological Activity of a Conformationally Constrained Chemotactic gamma–Lactam Formyl Tetrapeptide", Arzneim. Forsch., Bd. 46, Nr. 10, 1996, Seiten 964–966, XP002111930.

M. J. Deal et al.: "Conformationally Constrained Tachykinin Analogues: Potent and Highly Selective Neurokinin NK–2–Receptor Antagonists", J. Med. Chem., Bd. 35, Nr. 22, 1992, Seiten 4195–4204, XP002111931.

K. Barlos et al.: "Anwendung von N–Tritylmethionin zur Darstellung von biologisch und synthetisch interessanten Heterocyclen", Liebigs Ann. Chem., 1988, Seiten 1127–1134, XP002111932.

B.J. Williams et al.: "Cyclic Peptides as Selective Tachykinin Antagonists", J. Med. Chem., Bd. 36, Nr. 1, 1993, Seiten 2–10, XP002111933.

Y. Knobler et al.: "Lactam Formation through Aminolysis of alpha–Amino–gamma–butyrolacton. 2–Amino–4–hydroxybutyramides and 1–Aryl 3–Aminopyrrolidin–2–ones", J. Org. Chem., Bd. 29, Nr. 5, 1964, Seiten 1229–1236, XP002111934.

R. Laliberté, L. Berlinguet: "Synthèses d' acides aminobutyriques II. Acides alkylamino–2 hydroxy–4 butyriques", Can. J. Chem., Bd. 40, 1962, Seiten 1960–1964, XP002111935.

M. Kawai et al.: "CD spectra of DNP derivatives of aromatic aplha–amino acids and related compounds", Tetrahedron, Bd 34, 1978, Seiten 3435–3444, XP002111936.

S. P. L. Sörensen, A. C. Andersen: "Studien Über Aminosäuresynthesen. VIII. Diaminodicarbonsäuren und Oxyaminosäuren", Hoppe–Seyler's Z. Physiol. Chem., Bd. 56, 1908, Seiten 275–304, XP002111937.

P. Chocat et al.: "Synthesis of Selenocystine and Selenohomocystine with O–Acetylhomoserine Sulfhydrylase", Agric. Biol. Chem., Bd. 49, Nr. 4, 1985, Seiten 1143–1150, XP002111938.

S. Nagai, M. Flavin: "Acetylhomoserine", J. Biol. Chem., Bd. 242, Nr. 17, 1967, Seiten 3884–3895, XP002111939.

D. M. Kalvin, R. W. Woodward: "Synthesis of (4R)–D, L–'4–(2)H!–and (4S)–'4–(2)H!Homoserine Lactones", J. Org. Chem., Bd. 50, Nr. 13, 1985, Seiten 2259–2263, XP002111940.

N. Esaki et al.: "Reactions of O–Substituted L–Homoserines Catalyzed by L–Methionine gamma–Lyase and Their Mechanism", Agric. Biol. Chem., Bd. 48, Nr. 8, 1984, Seiten 1991–1996, XP002111941.

P. Malatesta et al.: "alpha–n–butilammino–beta–cloropropio(gamma–clorobutirro)anilidi ad attività anestetica locale", Ann. Chim. (Rome), Bd. 55, 1965, Seiten 133–142, XP002111942.

R. Sudo et al.: "Studies on gamma–butyrolactone derivatives. I Synthesis of alpha–amino–gamma–butyrolactone", Nippon Kagaku Zasshi, Bd. 74, 1953, Seiten 1009–11013, XP002111943.

J. E. Semple et al.: "Design, Synthesis, and Evaluation of a Novel, Selective, and Orally Bioavailable Class of Thrombin Inhibitors: 1–Argininal Derivatives Incorporating P3–P4 Lactam Sulfonamide Moieties", J. Med. Chem., Bd. 39, Nr. 23, 1996, Seiten 4531–4536, XP002081550.

Patent Abstracts of Japan, vol. 012, No. 312, 24. Aug. 1988 (1988–08–24) & JP 63 083082 A (Takeda Chem. Ind., Ltd.), 13. Apr. 1988 (1988–04–13).

& Chemical Abstracts, vol. 49, No. 10, 25. Mai 1955 (1955–05–25) Columbus, Ohio, US; abstract No. i, Spalte 6829.

* cited by examiner

PROCESS FOR THE PREPARATION OF 3-AMINO-2-OXO-PYRROLIDINES, NOVEL INTERMEDIATES AND THEIR USE

This application is a divisional of Ser. No. 09/860,568 May 21, 2001 abandoned which is a divisional of Ser. No. 09/316,150 May 21, 1999, now U.S. Pat. No. 6,281,364.

CROSS-REFERENCE TO RELATED APPLICATION

This application claims priority from German Application No. 198 22 912.7, filed on May 22, 1998, the subject matter of which is hereby incorporated herein by reference.

BACKGROUND OF THE INVENTION

1. Field of the Invention

The present invention relates to a process for the preparation of compounds of the general formula I and their salts

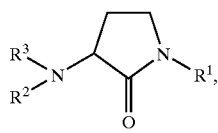

(I)

wherein
- $R^1$ may represent H, $(C_1–C_8)$-alkyl, $(C_2–C_8)$-alkenyl, $(C_2–C_8)$-alkynyl, $(C_2–C_8)$-alkoxyalkyl, $(C_1–C_8)$-acyl, which are optionally linear or branched and may be mono- or poly-substituted by halogens, by radicals containing N, O, P, S atoms, $(C_3–C_7)$-cycloalkyl, which may be saturated or unsaturated and mono- or poly-substituted by linear or branched $(C_1–C_8)$-alkyl, $(C_2–C_8)$-alkenyl, $(C_2–C_8)$-alkynyl, $(C_1–C_8)$-acyl, $(C_1–C_8)$-alkoxy, $(C_2–C_8)$-alkoxyalkyl, by halogens, by radicals containing N, O, P, S atoms, or may contain hetero atoms such as N, O, P, S in the ring, aryl, such as phenyl or naphthyl, aralkyl, such as benzyl or phenethyl, heteroaryl, such as furyl, pyrrolyl, pyridyl, heteroaralkyl, such as furfuryl, pyrrolylmethyl, pyridylmethyl, furylethyl, pyrrolylethyl, pyridylethyl, wherein the rings just mentioned may optionally be mono- or poly-substituted by linear or branched $(C_1–C_8)$-alkyl, $(C_2–C_8)$-alkenyl, $(C_2–C_8)$-alkynyl, $(C_1–C_8)$-acyl, $(C_1–C_8)$-alkoxy, $(C_2–C_8)$-alkoxyalkyl, by halogens, by radicals containing N, O, P, S atoms, N-bonded amino acid or peptide residue,
- $R^2$ may represent H, $(C_1–C_8)$-alkyl, $(C_2–C_8)$-alkenyl, $(C_2–C_8)$-alkynyl, $(C_2–C_8)$-alkoxyalkyl, which are optionally linear or branched and may be mono- or poly-substituted by halogens, by radicals containing N, O, P, S atoms, $(C_3–C_7)$-cycloalkyl, which may be saturated or unsaturated and mono- or poly-substituted by linear or branched $(C_1–C_8)$-alkyl, $(C_2–C_8)$-alkenyl, $(C_2–C_8)$-alkynyl, $(C_1–C_8)$-acyl, $(C_1–C_8)$-alkoxy, $(C_2–C_8)$-alkoxyalkyl, by halogens, by radicals containing N, O, P, S atoms, and/or may contain hetero atoms such as N, O, P, S in the ring, aryl, such as phenyl or naphthyl, aralkyl, such as benzyl or phenethyl, heteroaryl, such as furyl, pyrrolyl, pyridyl, heteroaralkyl, such as furfuryl, pyrrolylmethyl, pyridylmethyl, furylethyl, pyrrolylethyl, pyridylethyl, wherein the rings just mentioned may optionally be mono- or poly-substituted by linear or branched $(C_1–C_8)$-alkyl, $(C_2–C_8)$-alkenyl, $(C_2–C_8)$-alkynyl, $(C_1–C_8)$-acyl, $(C_1–C_8)$-alkoxy, $(C_2–C_8)$-alkoxyalkyl, by halogens, by radicals containing N, O, P, S atoms,
- $R^3$ may represent H, ClCO, $(C3–C_8)$-acyl, which may optionally be linear or branched, a C-bonded amino acid or peptide residue or a conventional peptide-protecting group such as, for example, formyl, carbamoyl, benzyloxycarbonyl, tert.-butyloxycarbonyl, allyloxycarbonyl, trifluoroacetyl.

The invention relates also to novel intermediates of the general formulae V, IV and II and their salts

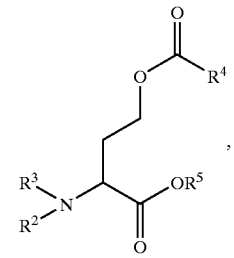

(V)

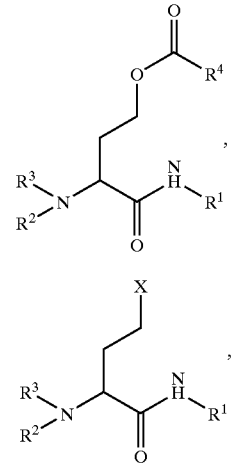

(IV)

(II)

wherein $R^1$, $R^2$, $R^3$ are as defined above and $R^4$ represents $(C_1–C_8)$-alkyl, $(C_2–C_8)$-alkenyl, $(C_2–C_8)$-alkoxy, $(C_2–C_8)$ alkenyloxy, which are optionally linear or branched and are optionally substituted by one or more halogen atoms, aryl, such as phenyl or naphthyl, aralkyl, such as benzyl or phenethyl, arylalkyloxy, such as benzyloxy, and $R^5$ represents H, or $R^5$ and $R^3$ are bonded together via a C=O group to form a ring, wherein in formula V, when $R^2$ is H, $R^3$ may not be H, and to the uses of those intermediates.

2. Background Information

The compounds that can be prepared by the process according to the invention and the novel intermediates are valuable intermediates for the production of biologically active substances. For example, 3-amino-2-oxo-pyrrolidines are preferably used as a structural unit for peptide mimetics, which are used as pharmaceuticals. In WO 94/22820, 3-amino-1-phenyl-2-oxo-pyrrolidines substituted at the phenyl ring, for example, are described as intermediates for thrombocyte aggregation inhibitors. Other biologically active compounds containing those γ-lactams have been studied by Kottirsch et al. (Bioorg. Med. Chem. Lett. 1993, 3, 1675). In other examples, they are used in highly potent neurokinin NK-2 receptor antagonists according to Deal et al. (J. Med. Chem. 1992, 35, 4195).

The majority of the processes used hitherto for the preparation of substituted 3-amino-2-oxo-pyrrolidines consist in first converting the corresponding open-chained methionine compounds into their sulfonium salts and cyclising the latter with strong bases in a suitable solvent. Friedinger et al. (J. Org. Chem. 1982, 47, 104–109) use for that purpose methyl iodide and sodium hydride, which is difficult to handle in a large-scale process. In U.S. Pat. No. 5,484,946, trimethylsulfonium or trimethylsulfoxonium salts are used for the alkylation instead of methyl iodide, which is readily volatile. The cyclisation is then carried out using potassium carbonate.

However, the main problem of those procedures, namely the unavoidable release from the methionine precursor of dimethyl sulfide, which is extremely strong-smelling, cannot be avoided in the process just mentioned either. Moreover, the necessary use of expensive aprotic polar solvents such as, for example, DMSO in the cyclisation with potassium carbonate appears to be a further disadvantage.

WO 94/22820 mentions a process in which racemic homoserine derivatives, which have been prepared starting from butyrolactone, are cyclised to pyrrolidones by means of triphenylphosphine and azodicarboxylic acid diesters. However, those reagents are not very suitable for use in an industrial process since they are relatively expensive. Moreover, the cyclisation in that variant yields a number of secondary products which are difficult and hence time-consuming and expensive to separate from the desired derivative (K. Nakajima et al. Peptide Chemistry 1983, 77–80).

Although L-homoserine is a naturally occurring amino acid, as yet there are known only a relatively small number of syntheses of homoserineamides, for example peptides, that start from homoserine. The reasons therefor are that homoserine and the corresponding N-acyl compounds very readily form the corresponding lactones under acid conditions (J. P. Greenstein, M. Winitz, "Chemistry of the Amino Acids", Wiley, N.Y. 1961, Vol. 3, p. 2612). The same also occurs when the carboxy group is activated, as is necessary for the preparation of homoserineamides.

Although it is possible to react also N-acylhomoserine-lactones with alkylamines and amino acid esters or amino acid salts to form the corresponding amides (Sheradsky et al., J. Org. Chem. 1961, 26, 2710), the reaction requires either very long reaction times or relatively high temperatures. For that reason, this method has not been used for the preparation of complex, optionally optically active compounds.

For the preparation of homoserineamides there are used homoserine derivatives in which the hydroxy function is protected by a suitable group. Hitherto, that was achieved either by a trityl group (Barlos et al., J. Chem. Soc., Chem. Commun. 1986, 1259), by mono- or di-methoxytrityl groups (Beltran et al., Lett. Pept. Sci. 1997, 4, 147), tert.-butyldimethylsilyl group (WO 97/46248) or benzyl groups (Cornille et al., J. Am. Chem. Soc. 1995, 117, 909). The disadvantage of those protecting groups is that they either require expensive chemicals or can be introduced only in a complicated manner.

O-Acyl compounds could be simple and inexpensive protecting groups. However, the problem with those compounds is that they very rapidly undergo an O->N-acyl shift under basic conditions, with formation of the corresponding N-acylhomoserines. Furthermore, for the preparation of O-acetylhomoserine there has hitherto been described only the reaction of homoserine with acyl anhydrides in perchloric acid which, on account of the explosive tendency of perchlorates, appears to be very disadvantageous and unsuitable for larger batches. The yields are only 51% at the most (Nagani et al., J. Biol. Chem. 1967, 242, 3884).

SUMMARY OF THE INVENTION

Accordingly, the object of the present invention is to provide a further process for the preparation of γ-lactams of the general formula I which can advantageously be carried out on an industrial scale, that is to say which avoids the use of critical substances and expensive reagents as far as possible. Within the context of the invention, critical substances are to be understood as being compounds which, when used on a large scale, give rise to particular risks as regards environmental pollution or health and safety at work.

Another object of the present invention is to provide a process which allows the γ-lactams of the general formula I to be prepared without formation of the foul-smelling dimethyl sulfide.

A further object of the invention is to provide novel intermediates which can advantageously be used for the synthesis of the γ-lactams of the general formula I, and to indicate an advantageous use of those intermediates.

These and other objects, which are not explained in greater detail but which readily follow from the prior art in an obvious manner, are the subject of a process having the features of the characterising clause of claim 1. Advantageous developments of the process according to the invention are described in the sub-claims which are dependent on claim 1. Claims 26 to 34 achieve the object of providing novel intermediates. In claim 35 there is described an advantageous use of the intermediates.

By synthesising a compound of the general formula I and its salts

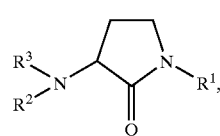

(I)

wherein

R$^1$ may represent H, (C$_1$–C$_8$)-alkyl, (C$_2$–C$_8$)-alkenyl, (C$_2$–C$_8$)-alkynyl, (C$_2$–C$_8$)-alkoxyalkyl, (C$_1$–C$_8$)-acyl, which are optionally linear or branched and may be mono- or poly-substituted by halogens, by radicals containing N, O, P, S atoms, (C$_3$–C$_7$)-cycloalkyl, which may be saturated or unsaturated and mono- or poly-substituted by linear or branched (C$_1$–C$_8$)-alkyl, (C$_2$–C$_8$)-alkenyl, (C$_2$–C$_8$)-alkynyl, (C$_1$–C$_8$)-acyl, (C$_1$–C$_8$)-alkoxy, (C$_2$–C$_8$)-alkoxyalkyl, by halogens, by radicals containing N, O, P, S atoms, and/or may contain hetero atoms such as N, O, P, S in the ring, aryl, such as phenyl or naphthyl, aralkyl, such as benzyl or phenethyl, heteroaryl, such as furyl, pyrrolyl, pyridyl, heteroaralkyl, such as furfuryl, pyrrolylmethyl, pyridylmethyl, furylethyl, pyrrolylethyl, pyridylethyl, wherein the rings just mentioned may optionally be mono- or poly-substituted by linear or branched (C$_1$–C$_8$)-alkyl, (C$_2$–C$_8$)-alkenyl, (C$_2$–C$_8$)-alkynyl, (C$_1$–C$_8$)-acyl, (C$_1$–C$_8$)-alkoxy, (C$_2$–C$_8$)-alkoxyalkyl, by halogens, by radicals containing N, O, P, S atoms, N-bonded amino acid or peptide residue, R$^2$ may represent H, (C$_1$–C$_8$)-alkyl, (C$_2$–C$_8$)-alkenyl, (C$_2$–C$_8$)-alkynyl, (C$_2$–C$_8$)-alkoxyalkyl, which are optionally linear or branched and may be mono- or poly-substituted by halogens, by radicals containing N, O, P, S atoms, (C$_3$–C$_7$)-cycloalkyl, which may be saturated or unsaturated and mono- or poly-substituted by linear or branched (C$_1$–C$_8$)-alkyl, (C$_2$–C$_8$)-alkenyl, (C$_2$–C$_8$)-alkynyl, (C$_1$–C$_8$)-acyl, (C$_1$–C$_8$)-alkoxy, (C$_2$–C$_8$)-alkoxyalkyl, by halogens, by radicals containing N, O, P, S atoms, and/or may contain hetero atoms such as N, O, P, S in the ring, aryl, such as phenyl or naphthyl, aralkyl, such as benzyl or phenethyl, heteroaryl, such as furyl, pyrrolyl, pyridyl, heteroaralkyl, such as furfuryl, pyrrolylmethyl, pyridylmethyl, furylethyl, pyrrolylethyl, pyridylethyl, wherein the rings just mentioned may optionally be mono- or poly-substituted by linear or branched $(C_1-C_8)$-alkyl, $(C_2-C_8)$-alkenyl, $(C_2-C_8)$-alkynyl, $(C_1-C_8)$-acyl, $(C_1-C_8)$-alkoxy, $(C_2-C_8)$-alkoxyalkyl, by halogens, by radicals containing N, O, P, S atoms, $R^3$ may represent H, ClCO, $(C_1-C_8)$-acyl, which may optionally be linear or branched, a C-bonded amino acid or peptide residue or a conventional peptide-protecting group such as, for example, formyl, carbamoyl, benzyloxycarbonyl, tert.-butyloxycarbonyl, allyloxycarbonyl, trifluoroacetyl, by cyclising derivatives of the general formula II

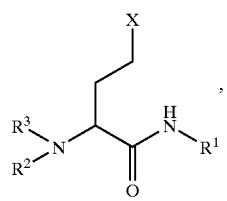

(II)

wherein $R^1$, $R^2$, $R^3$ are as defined above and X represents an element from the group halogen, sulfonic acid ester, the desired compounds of the general formula I are obtained in good yields in a very simple and nevertheless advantageous manner, the process according to the invention being predestined for a large-scale industrial process owing to the fact that the starting materials necessary for the synthesis are relatively inexpensive, the reaction is simple to perform, the yields are good, and dangerous or foul-smelling reagents are not used.

Within the context of the process according to the invention, a sulfonic acid radical X is to be understood as being any radical derived from a sulfonic acid of the structure $HOSO_3R'$, wherein R' in this connection represents a linear or branched $(C_1-C_8)$-alkyl radical or an aryl radical which may optionally be substituted by one or more $(C_1-C_8)$-alkyl radicals. The mentioned radicals may optionally be substituted by one or more elements from the group halogen, preferably Cl or F.

The above-described cyclisation may advantageously be carried out under basic conditions, it being possible to use as the base preferably an alkali hydroxide. The use of aqueous alkali hydroxide solution is especially preferred, and very special preference is given to the use of sodium hydroxide solution for the cyclisation. Compounds of the general formula II that can advantageously be used for the cyclisation possess a sulfonic acid ester as the leaving group X, and the use of the so-called mesyl ($OSO_3Me$) group is especially preferred.

This process can be applied very especially to compounds of the general formula II wherein $R^1$ is a p-cyanophenyl or p-carbamoylphenyl radical, while $R^2$ is advantageously H and $R^3$=benzyloxycarbonyl.

The cyclisation can be carried out at temperatures of from $-20°$ C. to $100°$ C. Temperatures of from $0°$ C. to $50°$ C. are preferably employed in the cyclisation, very especially temperatures of from $10°$ C. to $30°$ C.

The synthesis of the compounds of the general formula I can preferably and extremely simply be accomplished from compounds of the general formula II, if II is reacted to form I without being isolated beforehand.

The compounds of the general formula II can advantageously be prepared from derivatives of the general formula III

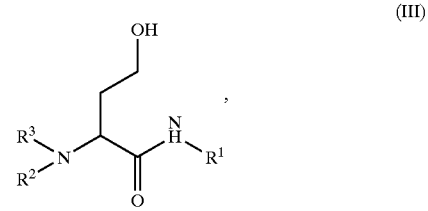

(III)

wherein $R^1$, $R^2$, $R^3$ are as defined above. The compounds of the general formula III are preferably not isolated before being processed further to form compounds of formula II.

The compounds of formula III, in turn, are very especially preferably prepared from compounds of the general formula IV

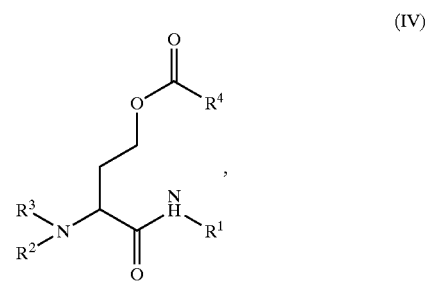

(IV)

wherein $R^1$, $R^2$, $R^3$ are as defined above and $R^4$ represents $(C_1-C_8)$-alkyl, $(C_2-C_8)$-alkenyl, $(C_1-C_8)$-alkoxy, $(C_2-C_8)$-alkenyloxy, which are optionally linear or branched and are optionally substituted by one or more halogen atoms, aryl, such as phenyl or naphthyl, aralkyl, such as benzyl or phenethyl, arylalkyloxy, such as benzyloxy.

In principle, any processes for hydrolysis known to the person skilled in the art can be used for the above-mentioned conversion. Advantageously, however, compounds of the general formula IV can be converted into compounds of the general formula III by aminolysis. Special preference is given in this connection to the use of ammonia as the amine; very especially preferably, ammonia can be employed in the form of its aqueous solution.

The compound of the general formula IV, in turn, can advantageously be prepared from compounds of the general formula V

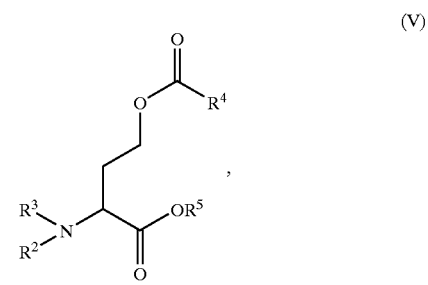

(V)

wherein $R^2$, $R^3_1$, $R^4$ are as defined above and $R^5$ represents H, or wherein $R^3$ and $R^5$ are bonded together via a C=O group to form a ring. Before they are reacted to form compounds of the general formula IV, compounds of the general formula V wherein $R^5$ is H can be activated preferably by means of acid chlorides (analogously to Houben-Weyl, Volume 15, Part 2, p. 169 ff). Compounds of the general formula V wherein $R^3$ and $R^5$ are bonded together via a C=O group to form a ring can advantageously be converted into compounds of the general formula IV wherein $R^3$ represents H.

According to the invention, the compounds of the general formula V can advantageously be prepared from the acid addition salts of the general formula VI

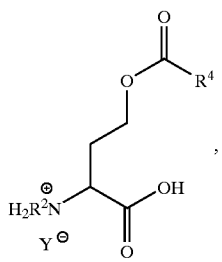

(VI)

wherein $R^2$, $R^4$ are as defined above and $Y\ominus$ is the corresponding base of an inorganic acid, by reaction with an acylating reagent derived from $R^3$. Within the scope of the invention, an inorganic acid is to be understood as being an acid whose pKa value is less than 2.5, such as, for example, HCl, HBr, $H_2SO_4$, $H_3PO_4$. Phosgene can preferably be used as the acylating reagent. In that case, compounds of the general formula V wherein $R^3$ and $R^5$ are bonded together via a C=O group to form a ring are obtained. Alternatively, compounds of the general formula VI can be obtained by reaction with acylating reagents from the group of the organic anhydrides, such as, for example, di-tert.-butyl pyrocarbonate, of the activated esters, such as, for example, trifluoroacetic acid ester, acetic acid hydroxysuccinimide ester, or of the halocarbonic esters, such as, for example, benzyloxycarbonyl chloride, allyloxycarbonyl chloride or tert.-butyloxycarbonyl fluoride. The above-described acylation can preferably take place in aqueous solution at a pH of from 4 to 9; it is especially preferred to maintain a pH range of from 6.5 to 7.5 in that reaction. The acylation to form compounds of the general formula V wherein $R^5$ is H can, however, also be carried out in organic solvents in the presence of a tertiary base. Triethylamine may advantageously be used as the tertiary base.

The acid addition salt of the general formula VI, in turn, can preferably be prepared from compounds of the general formula VII

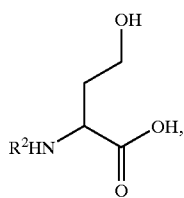

(VII)

wherein $R^2$ is as defined above. The reaction can take place in a mixture of a carboxylic acid $R^4COOH$ and the carboxylic acid chloride or bromide $R^4COCl$ or $R^4COBr$, respectively, wherein $R^4$ is as defined above. For that reaction it is advantageous first to mix together the appropriate carboxylic acid $R^4COOH$ and the corresponding carboxylic acid halide $R^4COHal$ and then to add the compound of the general formula VII to that mixture. The above-mentioned process is advantageously carried out at a temperature of from –20° C. to 50° C., preferably from –10° C. to 20° C. and especially from –5° C. to 10° C.

Another preferred variant for preparing the compound of the general formula V consists in reacting compounds of the general formula VIII

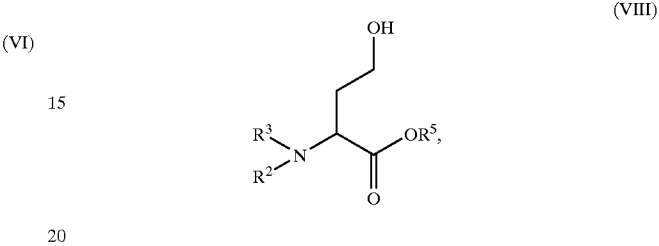

(VIII)

wherein the radicals $R^2$, $R^3$ may be as defined above and $R^5$ represents H, with the reagent $R^4COZ$, wherein $R^4$ is as defined above and Z represents an activating radical. The activating radical Z may in principle be any radical known to the person skilled in the art for that purpose, such as, for example, hydroxysuccinimide, hydroxybenzotriazole, $R^4CO^2$, halogen (The Chemical Synthesis of Peptides, J. Jones, Oxford Press 1991, p. 42 ff). For the acylation of the OH function of formula VIII there are preferably used compounds in which the activating radical Z corresponds to a halogen. In that case, the reaction is very especially preferably carried out in the carboxylic acid corresponding to the carboxylic acid halide as solvent. Especially preferred halides are the chlorides or bromides of the carboxylic acid. Very special preference is given to the embodiment in which the inorganic acid formed in the acylation is buffered by addition of the sodium-salt of the corresponding carboxylic acid used as solvent.

In a further aspect of the present invention, advantageous novel intermediates of the general formulae V, IV and II and their salts are provided

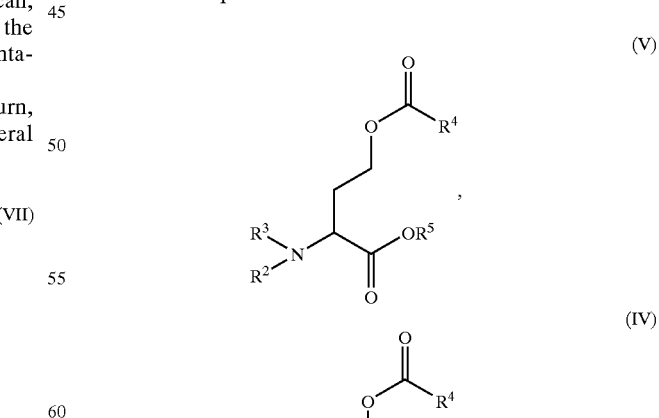

(V)

(IV)

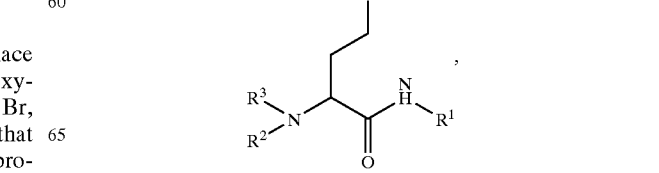

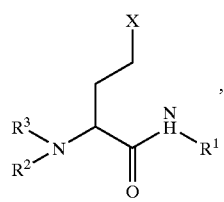

wherein $R^1$, $R^2$, $R^3$, $R^4$, $R^5$ are as defined above, wherein in formula V, when $R^2$ is H, $R^3$ may not be H. Preference is given to compounds in which $R^2$ is hydrogen, $R^3$ is a benzyloxycarbonyl, tert.-butyloxycarbonyl or trifluoroacetyl radical, $R^4$ is a methyl radical and $R^5$ is hydrogen, or in which $R^3$ and $R^5$ are bonded together via a C=O group to form a ring. X is preferably a halogen or a sulfonic acid ester, very especially preferably an $OSO_3Me$ group. $R^1$ is very especially preferably p-cyanophenyl or p-carbamoylphenyl.

The advantageous compounds of the general formulae V, IV and II are used according to the invention for the preparation of intermediates of biologically active substances.

The present invention is explained again in the scheme below:

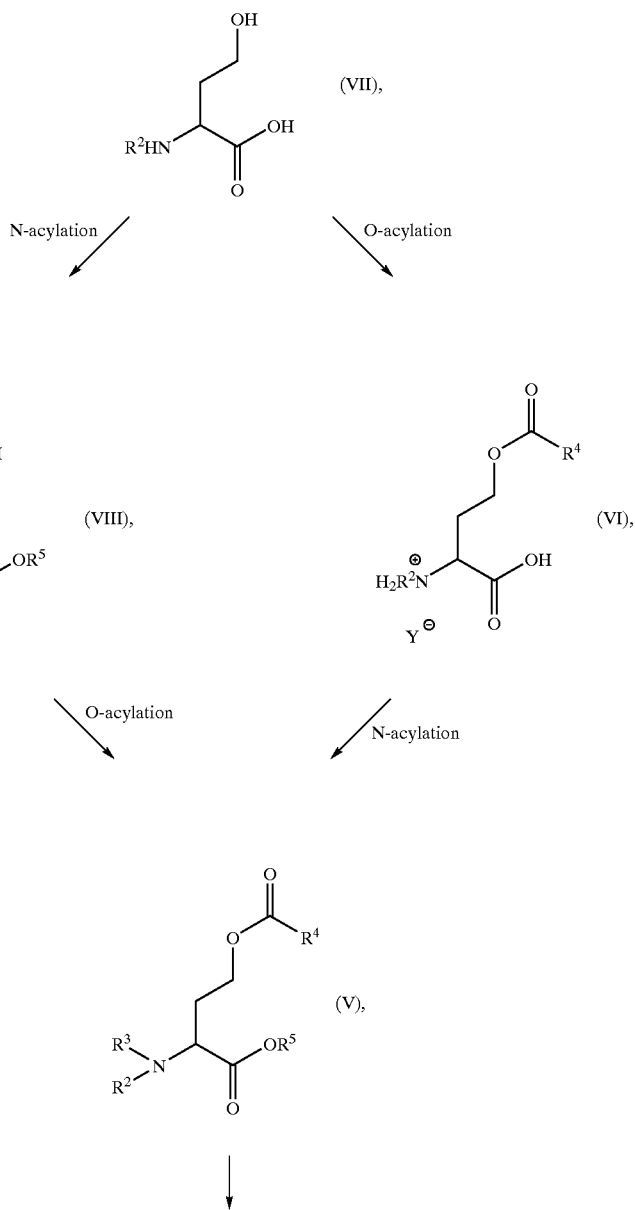

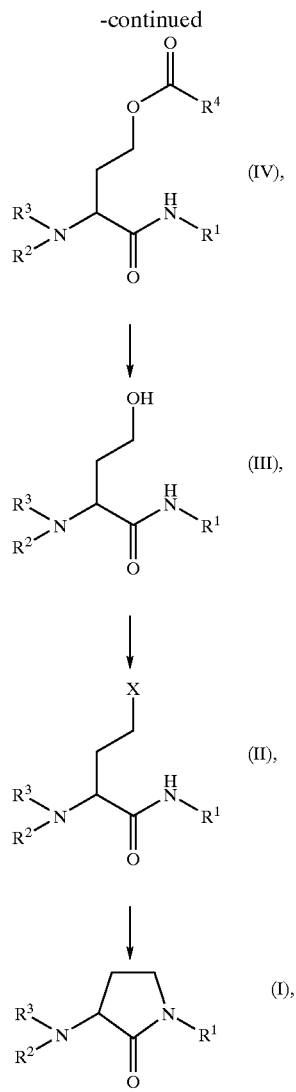

The cyclisation of II to I is an intramolecular nucleophilic substitution. In principle, any variant known to the person skilled in the art may be employed for that reaction. However, a number of subsidiary products, such as, for example, the removal or substitution of the leaving group, are to be expected in that reaction. For that reason it was very surprising that it was possible to find for the cyclisation, with the choice of leaving groups X, conditions that permit the use of a relatively strong base—in this case sodium hydroxide—in the presence of a polar protic, cation-stabilising solvent—in this case water—and nevertheless allow the reaction to proceed as selectively as possible. Those very inexpensive, uncritical reagents, which can readily be used for a large-scale process, are clearly to be preferred over other conditions from the prior art for the intramolecular substitution (dimethyl sulfide is not formed, sodium hydride is not used, no expensive reagents and solvents are required). A further advantage of those preferred reaction conditions is that the optical activity of enantiomerically enriched starting compounds is maintained virtually completely under the conditions according to the invention.

In the above-described reaction there are preferably used derivatives of II that contain the p-cyanophenyl or p-carbamoylphenyl group as the radical $R^1$, H as $R^2$, and a benzyloxycarbonyl radical as $R^3$. They yield advantageous compounds for the preparation of pharmaceuticals, as described, for example, in WO 94/22820.

The preparation of the compounds of formula II from III can be carried out analogously to processes known from the literature. It is, however, preferred to form a sulfonic acid ester from III and sulfonic acid chloride, which ester can advantageously be reacted further in the manner indicated above, without being isolated as an intermediate, to form I. Special preference is given to the use of the mesyl ($OSO_3Me$) group, which can be introduced using mesyl chloride and triethylamine as base. It is astonishing that under the preferred reaction conditions according to the invention it is not the hydrolysis of the sulfonic acid ester II but the cyclisation that is the main reaction. That was not foreseeable. It is also especially advantageous that the compounds of the general formula II do not have to be isolated before they are reacted to form I. They are formed and then preferably reacted in situ.

The preparation of the compounds of the general formula III from the compounds of the general formula IV can be carried out by acid or basic hydrolysis of the O-acyl group. Under those conditions, however, partial hydrolysis, for example of the N-acyl group which may be present and of the amide bond, may occur. Under the preferred hydrolysis variant, therefore, the removal of the O-acyl group is carried out by aminolysis. Ammonia is especially preferably used for that purpose, very especially preferably its aqueous solution. Under those conditions, the O-acyl group is removed selectively.

According to the invention it is also not necessary to isolate the compounds of the general formula III. They can also be reacted directly to form compounds of the general formula II. For the present process it is, therefore, extremely advantageous to select a process variant in which, starting from derivatives of the general formula IV to the end product of the general formula I, no intermediate stage is isolated intermediately. Nevertheless, the derivatives of the general formula I are obtained in good to very good yields and with a very high degree of purity. That was surprising and could in no way be foreseen; it is, however, all the more advantageous for a large-scale process since the very cost-intensive handling of isolated intermediate products can be reduced to a minimum.

There may be used as solvents for the conversion of III→II any organic solvents that are inert under the given conditions. Special preference is given to ethers, such as, for example, methyl tert.-butyl ether, tetrahydrofuran, dimethoxyethane, dioxane, hydrocarbons, such as, for example, hexane, cyclohexane, toluene, ketones, such as,. for example, acetone, diethyl ketone, methyl isobutyl ketone, and carboxylic acid alkyl esters, such as, for example, ethyl acetate, isopropyl acetate, n-butyl acetate. Very special preference is given to organic solvents that form a low-boiling azeotrope with water, such as, for example, toluene, methyl isobutyl ketone or n-butyl acetate.

Compounds of formula IV, in turn, can preferably be obtained from derivatives V. In the case where-the radicals $R^3$ and $R^5$ are bonded together via a C=O group to form a ring, that is to say an N-carboxylic acid anhydride of the derivative in question is present, the carboxy function of the homoserine derivative does not have to be activated for the coupling. The derivatives are then simply reacted with the chosen amine, yielding compounds of formula IV wherein $R^3$ is H. The latter can be converted into the corresponding N-acyl compounds in accordance with processes known from the literature by reaction with an acylating reagent derived from $R^3$.

In the case where $R^5$=H, the carboxy function is activated before coupling with the amine. That is effected by methods of peptide chemistry known to the person skilled in the art (Houben-Weyl, Volume 15, 2nd part), such as, for example, via mixed anhydrides, activated esters, etc. Reaction with an acid chloride, such as, for example, pivaloyl chloride, to form the mixed anhydride is, however, preferred.

The compounds of the general formula V according to the invention can be obtained from homoserine derivatives such as VII by two different methods. Either VII is first acylated at the oxygen to form VI and then processed further at the nitrogen by N-acylation to form V, or compounds of the general formula VIII, which are obtainable from VII by N-acylation, are converted into V by O-acylation.

The N-acylation to form the homoserine derivative VIII can be carried out analogously to that of other amino acids (Houben-Weyl, Volume 15, Part 1 and Part 2). In principle there may be used as the acylating reagents any acylating reagents derived from $R^3$, such as amino-protecting reagents, C-terminal activated amino acids or peptides.

In the isolation of the N-acylhomoserines of formula VIII there was, however, the problem that those compounds, as the free acid, are very unstable and readily cyclise to form the corresponding lactones. That cyclisation is catalysed by acids and, moreover, always occurs when the acid function is activated. It takes place also in the reaction with the activated acid derivative $R^4COZ$ under the basic conditions which are otherwise customary for acylations. However, if the O-acylation is carried out in, as solvent, the carboxylic acid $R^4COOH$ corresponding to the reagent $R^4COZ$ used for the O-acylation, then the desired derivatives V are obtained almost exclusively. Special preference is given to the use of Cl for Z. A base is optionally and advantageously used to buffer the acid that forms during the reaction. The sodium salt of the carboxylic acid used as solvent is advantageously added as the base. The subsidiary product, the lactone, which is also formed in that process but to a lesser extent can be separated from the product mixture in a simple manner by extraction and, after ring-opening, is available for the reaction again.

In the second variant, the O-acylation to form derivatives VI is carried out according to the invention in a medium that helps to prevent the N-acylation, since that would be the more rapid reaction. The reaction is, therefore, preferably carries out in a carboxylic acid such as $R^4COOH$, to which the appropriate corresponding carboxylic acid halide, preferably carboxylic acid chloride, has previously been added. When the homoserine derivative VII is subsequently added, protection of the amino function of VII takes place by protonation as a result of the strong inorganic acid that forms in the solvent, and acylation of the hydroxy function preferentially occurs. The acid addition salt of the hydroxy-protected homoserine VI is therefore obtained as the product. The use of the dangerous perchloric acid, as is known from the prior art, is thus avoided. Furthermore, the yields in the process according to the invention are markedly better.

The further reaction of derivatives VI to form V can in principle be carried out by processes known to the person skilled in the art using an acylating reagent derived from $R^3$, such as amino-protecting reagents, C-terminal activated amino acids, peptides, or using phosgene. There was the problem, however, that the O-acylhomoserines VI rapidly undergo an O→N-acyl shift under basic conditions. According to the process of the invention, that can be avoided by maintaining the pH range, if the acylation is carried out in an aqueous medium, at from 3 to 9, preferably from 6 to 7.5. A further possibility is to react the O-acyl compounds VI in anhydrous solvents and triethylamine as base. For the reaction with phosgene, the acid addition salt VI can be used without addition of a base.

There come into consideration as linear or branched $(C_1-C_8)$-alkyl radicals methyl, ethyl, n-propyl, isopropyl, n-butyl, isobutyl, sec.-butyl, tert.-butyl, pentyl, hexyl, heptyl or octyl, including all possible isomers of constitution. The linear or branched $(C_2-C_8)$-alkenyl radical includes all the substituents.listed above in connection with the $(C_1-C_8)$-alkyl radical with the exception of the methyl radical, at least one double bond being present in those radicals. The scope of $(C_2-C_8)$-alkynyl corresponds to that of $(C_2-C_8)$-alkenyl, but at least one triple bond must be present in that case. The radical $(C_1-C_8)$-alkoxy corresponds to the radical $(C_1-C_8)$-alkyl, with the proviso that it is bonded to the ring via an oxygen atom. $(C_2-C_8)$-Alkoxyalkyl radicals are radicals in which the alkyl chain is interrupted by at least one oxygen function, wherein two oxygens may not be bonded together. The number of carbon atoms indicates the total number of carbon atoms contained in the radical. $(C_2-C_8)$-Alkenyloxy is to be understood as meaning radicals such as $(C_2-C_8)$-alkoxy that have at least one C-C double bond. Radicals containing N, O, P, S atoms are especially alkyl, alkenyl, alkynyl radicals of the above-mentioned type that have one or more of those hetero atoms in their chain or that are bonded to the molecule via one of those hetero atoms. ($C_3$–$C_7$)-Cycloalkyl is to be understood as being cyclopropyl, cyclobutyl, cyclopentyl, cyclohexyl or cycloheptyl radicals.

There are suitable as halogens fluorine, chlorine, bromine and iodine.

An N-bonded amino acid or peptide residue is to be understood as being a compound in which the molecule in question is bonded via its N atom to the α-carbon atom of a carboxylic acid derived from an amino acid, which carboxylic acid may be part of a peptide residue.

A C-bonded amino acid or peptide residue is to be understood as being a compound in which the molecule in question is bonded via its N atom to the carbon atom of the carboxyl group of an amino acid, which may be part of a peptide.

($C_1$–$C_8$)-Acyl is to be understood as being an alkyl radical having from one to eight carbon atoms, which may be linear or branched, that is to say which likewise includes all the possible isomers of constitution, and which is bonded to the molecule via a C=O function.

Within the scope of the invention, compounds having a stereogenic centre mean racemates as well as the enantiomeric antipodes of those structures. However, for the process according to the invention it is preferred to use enantiomerically enriched homoserine derivatives of the general formula VII. Thus, when the enantiomerically enriched starting materials (D or L) are used, the ID enantiomerically enriched products of the general formulae V and I (D or L) are obtained with virtually complete stereoconservation.

Salts are to be understood as being ionic addition compounds from strong acids such as HCl, HBr, $H_2SO_4$, $H_3PO_4$, $CF_3COOH$, p-toluenesulfonic acid, methanesulfonic acid and the molecule in question.

DETAILED DESCRIPTION OF THE INVENTION

The Examples which follow are intended to explain the invention.

EXAMPLES

O-Acetyl-L-homoserine Hydrochloride (VI)

72 g (0.60 mol) of L-homoserine are added in portions to a solution of 500 ml of acetic acid and 500 ml of acetyl chloride while cooling at <30° C. After 2 hours' stirring, no homoserine can be detected by TLC. The precipitate is filtered off with suction and washed with acetic acid. Drying in vacuo yields 90.1 g (75%) of O-acetyl-L-homo-serine hydrochloride.

M.p.: 133–135° C.;

$^1$H-NMR (DMSO): 2.01 (s, 3H), 2.16 (q, 2H), 3.94 (t, 1H), 4.15 (m, 2H), 8.61 (s, 3H), 13.82 (s, 1H).

N-Benzyloxycarbonyl-O-acetyl-L-homoserine (V)
a) From O-Acetyl-L-homoserine Hydrochloride (VI)

19.8 g (0.10 mol) of O-acetyl-L-homoserine hydrochloride are dissolved in 200 ml. of water, and 35.0 g (0.42 mol) of sodium hydrogen carbonate are added at 0° C. 19.2 g (0.11 mol) of benzyl chloroformate are then added and stirring is carried out for 3 hours at room temperature. The mixture is then extracted twice using 100 ml of methyl isobutyl ketone each time, and the aqueous phase is adjusted to pH=2 using concentrated hydrochloric acid and extracted twice using 150 ml of methyl isobutyl ketone (MIBK) each time. The combined organic phases are washed with 50 ml of saturated sodium chloride solution and concentrated in vacuo. 27.5 g (93%) of N-benzyloxy-carbonyl-O-acetyl-L-homoserine are obtained in the form of a colourless oil.

$^1$H-NMR (DMSO): 1.89 (m, 1H), 1.99 (s, 3H), 2.05 (m, 1H), 4.06 (m, 3H), 5.04 (s, 2H), 7.35 (m, 5H), 7.63 (d, 1H), 12.70 (s, 1H).

b) From N-Benzyloxycarbonyl-L-homoserine (VIII)

1.27 g (5 mmol) of N-benzyloxycarbonyl-L-homoserine are dissolved in 5 ml of acetic acid, and 0.41 g (5 mmol) of sodium acetate is added. 1.19 g (15 mmol) of acetyl chloride are then added and stirring is carried out for one hour. The acetic acid and the excess acetyl chloride are removed in vacuo, the residue is taken up in 30 ml of methyl isobutyl ketone and 30 ml of water, and the pH is adjusted to 8 using 50% sodium hydroxide solution. The aqueous phase is separated off, adjusted to pH=2 using hydrochloric acid and extracted using 30 ml of methyl iso-butyl ketone. Concentration of the organic phase in vacuo yields 0.99 g (67%) of N-benzyloxycarbonyl-O-acetyl-L-homoserine in the form of a colourless oil.

O-Acetyl-L-homoserine-N-carboxy Anhydride (V)

48.0 g (0.54 mol) of phosgene are introduced into a suspension of 32.2 g (0.16 mol) of O-acetyl-L-homoserine hydrochloride in 180 ml of tetrahydrofuran. The mixture is then heated until boiling for 30 minutes and the solvent is removed in vacuo. 29.2 g (98%) of O-acetyl-L-homoserine-N-carboxy anhydride are obtained in the form of a colourless oil.

$^1$H-NMR (DMSO): 1.97 (s, 3H), 2.07 (dd, 2H), 4.11 (t, 2H), 4.54 (t, 1H), 9.12 (s, 1H).

O-Acetyl-L-homoserine p-cyanoanilide (IV)

29.2 g (0.16 mol) of O-acetyl-L-homoserine-N-carboxy anhydride dissolved in 100 ml of DMF are added to a suspension of 24.7 g (0.16 mol) of aminobenzonitrile hydrochloride in 150 ml of DMF, and stirring is carried out for 24 hours at room temperature. Removal of the solvent in vacuo yields an oil, which is reacted further without further purification.

$^1$H-NMR (DMSO): 1.87 (s, 3H), 2.22 (m, 2H), 4.16 (m, 2H), 4.23 (t, 1H), 7.82 (d, 2H), 7.92 (d, 2H).

N-Benzyloxycarbonyl-O-acetyl-L-homoserine p-cyanoanilide (IV)

a) From N-Benzyloxycarbonyl-O-acetyl-L-homoserine (V)

24.0 g (0.045 mol) of N-benzyloxycarbonyl-O-acetyl-L-homo-serine are dissolved in 75 ml of tetrahydrofuran; 6.2 ml (0.045 mol) of triethylamine are added and the mixture is cooled to 0° C. 5.65 ml (0.045 mol) of pivaloyl chloride are added and stirring is carried out for 15 minutes at that temperature. After the addition of 5.9 g (0.045 mol) of p-aminobenzonitrile, stirring is carried out for 24 hours without cooling. After removal of the tetrahydrofuran in vacuo, the residue is taken up in 100 ml of MIBK and 50 ml of water, the pH is adjusted to 2 using concentrated hydrochloric acid, and the phases are separated. The organic phase is washed again with 50 ml of water; a further 50 ml of water are added and the pH is adjusted to 12 using 50% sodium hydroxide solution. The organic phase is separated off, washed with 50 ml of water and concentrated in vacuo. 100 ml of methyl tert.-butyl ether are added to the residue, and the precipitate is filtered off with suction. Drying in vacuo yields 9.2 g (52%) of N-benzyl-oxycarbonyl-O-acetyl-L-homoserine p-cyanoanilide.

M.p.: 76–78° C.;

$^1$H-NMR (DMSO): 1.94 (s, 3H), 1.96 (m, 1H), 2.06 (m, 1H), 4.09 (t, 2H), 4.29 (m, 1H), 5.05 (s, 2H), 7.34 (m, 5H), 7.80 (m, 5H), 10.53 (s, 1H).

b) From O-Acetyl-L-homoserine p-Cyanoanilide Hydrochloride (IV)

18.1 g (104 mmol) of benzyl chloroformate are added at 0° C. to 17.5 g (80 mmol) of O-acetyl-L-homoserine p-cyanoanilide hydrochloride and 34 g (400 mmol) of sodium carbonate in 150 ml of water, and stirring is carried out for 14 hours. The resulting precipitate is filtered off and dissolved in 120 ml of methyl isobutyl ketone and 50 ml of water, and the solution is adjusted to pH 2 using concentrated hydrochloric acid. The organic phase is separated off, washed with 30 ml of water and concentrated in vacuo. The residue is stirred with 200 ml of methyl tert.-butyl ether and filtered off with suction. 16.9 g (53%) of N-benzyloxycarbonyl-O-acetyl-L-homosetine p-cyanoanilide are obtained.

N-Benzyloxycarbonyl-L-homoserine p-Cyanoanilide (III)

14.0 g (0.035 mol) of N-benzyloxycarbonyl-O-acetyl-L-homo-serine p-cyanoanilide are dissolved in 140 ml of methanol; 14 ml of 25% ammonia are added and the mixture is heated for 4 hours at 60° C. Concentration is carried out in vacuo, and 100 ml of methyl tert.-butyl ether are added to the residue. The precipitate is filtered off with suction and dried in vacuo. 8.7 g of N-benzyloxycarbonyl-L-homoserine p-cyanoanilide are obtained.

M.p. : 125–128° C.;

$^1$H-NMR (DMSO): 1.78 (m, 1H), 1.86 (m, 1H), 4.49 (dt, 2H), 4.27 (m, 1H), 4.61 (t, 1H), 5.03 (s, 2H), 7.37 (m, 5H), 7.61 (d, 1H), 7.79 (dd, 4H), 10.45 (s, 1H).

3-Benzyloxycarbonyl-amino-1-(4-cyanophenyl)-2-oxo-pyrrolidine (I)

a) Using Mesyl Chloride/triethylamine 31.0 g (0.27 mol) of mesyl chloride are added at –10° C. to 63.6 g (0.18 mol) of N-benzyloxycarbonyl-L-homoserine p-cyanoanilide in 600 ml of tetrahydrofuran, and 37.4 ml (0.27 mol) of triethylamine are added dropwise over a period of 15 minutes in such a manner that the temperature remains below –5° C. The mixture is stirred for one hour at –10° C., then 54 g of 50% sodium hydroxide solution are added and stirring is carried out for 12 hours at room temperature. One litre of water is then added and the pH is adjusted to 8 using concentrated hydrochloric acid. The product obtained after removal of the tetrahydrofuran in vacuo is filtered off with suction. For further purification, the crude product is stirred with one litre of MIBK. Drying yields 38.6 g (64% of the theoretical yield) of 3-benzyloxycarbonyl-amino-1-(4-cyanophenyl)-2-oxo-pyrrolidine.

M.p.: 192–196° C.;

$^1$H-NMR (DMSO): 2.02 (m, 1H), 2.41 (m, 1H), 3.78 (m, 1H), 3.84 (m, 1H), 4.47 (m, 1H), 5.07 (s, 2H), 7.33, 7.38 (m, 5H), 7.77 (d, 1H), 7.88 (dd, 4H).

b) Using Tosyl Chloridelpyridine 1.0 g (2.8 mmol) of N-benzyloxycarbonyl-L-homoserine p-cyanoanilide in 10 ml of pyridine are added to 0.59 g (3.1 mmol) of tosyl chloride, and stirring is carried out for one hour at room temperature. The pyridine is removed in vacuo, the residue is dissolved in 20 ml of tetrahydrofuran, and 1 g of 50% NaOH is added. The mixture is stirred overnight, and then 20 ml of water are added and the tetrahydrofuran is removed in vacuo. The precipitate is filtered off with suction and washed with MIBK. 0.44 g (47%) of 3-benzyloxycarbonyl-amino-1-(4-cyanophenyl)-2-oxo-pyrrolidine is obtained.

Preparation of 3-Amino-i-(4-cyanophenyl)-2-oxo-pyrrolidine hydrochloride (I)

50 g (0.15 mol) of 3-benzyloxycarbonyl-amino-1-(4-cyano-phenyl)-2-oxo-pyrrolidine are suspended in 600 ml of methanol, and 14.1 ml of 36% hydrochloric acid are added. After the addition of 2.5 g of 5% palladium on activated carbon, hydrogen is passed through at 45° C. After 40 minutes, the mixture is cooled, the catalyst is filtered off and the filtrate is concentrated to dryness. Recrystallisation from methanol/isopropanol yields 28.5 g (80%) of 3-amino-1-(4-cyanophenyl)-2-oxo-pyrrolidine hydrochloride.

M.p.: 256–258° C. (decomp.);

$^1$H-NMR (DMSO): 2.20 (m, 1H), 2.55 (m, 1H), 3.87 (dt, 1H), 3.97 (t, 1H); 4.27 (dd, 1H), 7.91 (s, 4H), 8.89 (s, 3H).

Preparation of 3-Benzyloxycarbonyl-amino-1-(4-cyanophenyl)-2-oxo-pyrrolidine (I) from O-Acetyl-L-homoserine Hydro-chloride (VI) Without Isolation of the Intermediate Stages 1883 g (9.52 mol) of O-acetyl-L-homoserine hydrochloride are added to a solution of 1600 g (19.04 mol) of sodium hydrogen carbonate in 9.3 litres of water, and the mixture is cooled to 5° C. 1823 g (10.47 mol) of benzyl chloro-formate are then added and the pH is maintained at 7.5 by addition of 20% sodium carbonate solution. The mixture is stirred for 2 hours at 15° C. and then extracted using 20 litres of methyl isobutyl ketone. The aqueous phase is adjusted to pH=2.0 using concentrated hydrochloric acid and extracted twice using a total of 25 litres of methyl isobutyl ketone. The combined organic phases are washed with 3.5 litres of water and concentrated in vacuo. The residue is taken up in 19.5 litres of methyl isobutyl ketone; 856 g (8.47 mol) of triethylamine are added and the mixture is cooled to 0° C. 1042 g (8.47 mol) of pivaloyl chloride are then added and stirring is carried out for 20 minutes. After the addition of 1000 g (8.47 mol) of p-aminobenzonitrile, stirring is carried out for 36 hours at room temperature. 10 litres of water are then added and the pH is adjusted to 2.0 using concentrated hydrochloric acid. The organic phase is separated off; 10 litres of water are added and the pH is adjusted to 11 using 50% sodium hydroxide solution. After washing with 3 litres of water, the organic phase is concentrated in vacuo to about 3.5 kg. The residue is dissolved in 25 litres of methanol, and 7.5 litres of 25% ammonia are added. The mixture is then heated at 60° C. for 6 hours and then concentrated in vacuo. The residue is dehydrated by removal of 3×7.5 litres of methyl isobutyl ketone by distillation, is taken up in 25 litres of tetrahydrofuran and cooled to –5° C., and 1522 g (13.28 mol) of mesyl chloride are added. 1341 g (13.28 mol) of triethylamine are then added over a period of 45 minutes and stirring is carried out for one hour; then 2300 g of 50% sodium hydroxide solution are added and stirring is carried out for one hour. 3 litres of water are then added to the reaction mixture, and the pH is adjusted to 7 using concentrated hydrochloric acid. The solid obtained after removal of the tetrahydrofuran in vacuo is stirred with 14 litres of water, filtered off with suction and washed with water. The crude product is stirred with 19 litres of methyl isobutyl ketone at 50° C. and filtered off with suction. Drying yields 1401 g (44%) of 3-benzyloxy-carbonyl-amino-1-(4-cyanophenyl)-2-oxo-pyrrolidine.

N-Boc-O-acetyl-L-homoserine (V)

10.1 g (100 mmol) of triethylamine are added dropwise in the course of one hour to a suspension of 9.9 g (50 mmol) of O-acetyl-L-homoserine hydrochloride and 21.8 g (100 mmol) of Boc anhydride in 100 ml of tetrahydrofuran, and stirring is carried out for 12 hours at room temperature. After the addition of 100 ml of water, the tetra-hydrofuran is distilled off in vacuo, the pH is adjusted to 2 using concentrated hydrochloric acid, and the mixture is extracted twice using 100 ml of methyl isobutyl ketone each time. Concentration of the solution in vacuo yields 12.1 g (92%) of N-Boc-O-acetyl-L-homoserine in the form of a colourless oil.

$^1$H-NMR (DMSO): 1.38 (s, 9H), 1.84 (m, 1H), 1.99 (m, 1H), 1.99 (s, 3H), 4.00 (m, 3H), 7.11 (d, 1H).

N-Trifluoroacetyl-O-acetyl-L-homoserine (V)

7.6 g (55 mol) of potassium carbonate are added to a suspension of 9.9 g (50 mmol) of O-acetyl-L-homoserine hydrochloride and 7.8 g (55 mmol) of trifluoroacetylacetic acid ethyl ester in 200 ml of ethanol, and stirring is carried out for 14 hours. 10.8 g (110 mmol) of 37% hydrochloric acid and 200 ml of water are then added. The product obtained after removal of the ethanol by distillation is filtered off with suction, washed with water and dried. 5.8 g (45%) of N-trifluoroacetyl-O-acetyl-L-homo-serine are obtained.

M.p.: 134–136° C.;

$^1$H-NMR (DMSO): 1.99 (s, 3H), 2.04 (m, 1H), 2.19 (m, 1H), 4.06 (t, 2H), 4.37 (m, 1H), 9.73 (d, 1H), 13.08 (s, 1H).

What is claimed is:

1. A compound of the formula II or their salts

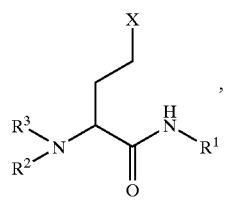

(II)

wherein:
$R^1$ may represent H,
$(C_1-C_8)$-alkyl,
$(C_2-C_8)$-alkenyl,
$(C_2-C_8)$-alkynyl,
$(C_2-C_8)$-alkoxyalkyl,
$(C_1-C_8)$-acyl, which are optionally linear or branched and may be mono- or poly-substituted by halogens, and by radicals containing N, O, P, or S atoms,
$(C_3-C_7)$-cycloalkyl, which may be saturated or unsaturated and mono- or poly-substituted by linear or branched $(C_1-C_8)$-alkyl, $(C_2-C_8)$-alkenyl, $(C_2-C_8)$-alkynyl, $(C_1-C_8)$-acyl, $(C_1-C_8)$-alkoxy, $(C_2-C_8)$-alkoxyalkyl, by halogens, by radicals containing N, O, P, or S atoms, and/or may contain hetero atoms such as N, O, P, or S in the ring,
aryl,
aralkyl,
heteroaryl,
heteroaralkyl, wherein the rings may optionally be mono- or poly-substituted by linear or branched $(C_1-C_8)$-alkyl, $(C_2-C_8)$-alkenyl, $(C_2-C_8)$-alkynyl, $(C_1-C_8)$-acyl, $(C_1-C_8)$-alkoxy, $(C_2-C_8)$-alkoxyalkyl, by halogens, and by radicals containing N, O, P, or S atoms,
N-bonded amino acid, or peptide residue;
$R^2$ may represent H,
$(C_1-C_8)$-alkyl,
$(C_2-C_8)$-alkenyl,
$(C_2-C_8)$-alkynyl,
$(C_2-C_8)$-alkoxyalkyl, which are optionally linear or branched and may be mono- or poly-substituted by halogens, and by radicals containing N, O, P, or S atoms,
$(C_3-C_7)$-cycloalkyl, which may be saturated or unsaturated and mono- or poly-substituted by linear or branched $(C_1-C_8)$-alkyl, $(C_2-C_8)$-alkenyl, $(C_2-C_8)$-alkynyl,
$(C_1-C_8)$-acyl, $(C_1-C_8)$-alkoxy, $(C_2-C_8)$-alkoxyalkyl, by halogens, by radicals containing N, O, P, or S atoms, and/or may contain hetero atoms such as N, O, P, or S in the ring,
aryl,
aralkyl,
heteroaryl,
heteroaralkyl, wherein the rings may optionally be mono- or poly-substituted by linear or branched $(C_1-C_8)$-alkyl, $(C_2-C_8)$-alkenyl, $(C_2-C_8)$-alkynyl, $(C_1-C_8)$-acyl,
$(C_1-C_8)$-alkoxy, $(C_2-C_8)$-alkoxyalkyl, by halogens, and by radicals containing N, O, P, or S atoms;
$R^3$ may represent H,
ClCO,
$(C_1-C_8)$-acyl, which may optionally be linear or branched,
a C-bonded amino acid or a peptide residue or a conventional peptide-protecting group;
and X represents an element from the group halogen, sulfonic acid ester.

2. The compound of formula II wherein $R^2$ is H, $R^3$ is benzyloxycarbonyl or tert.-butyloxycarbonyl or trifluoroacetyl, and X is a sulfonic acid ester.

3. The compound of formula II

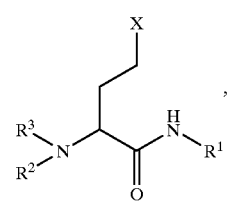

(II)

wherein $R^2$ is H, $R^3$ is benzyloxycarbonyl, X is the $OSO_3Me$ group, and $R^1$ is p-cyanophenyl or p-carbamoylphenyl.

4. A method of preparation of intermediates for biologically active substances with the compound according to claim 1.

* * * * *